United States Patent [19]

Kosaka

[11] Patent Number: 5,444,527
[45] Date of Patent: Aug. 22, 1995

[54] IMAGING FLOW CYTOMETER FOR IMAGING AND ANALYZING PARTICLE COMPONENTS IN A LIQUID SAMPLE

[75] Inventor: Tokihiro Kosaka, Kakogawashi, Japan

[73] Assignee: Toa Medical Electronics Co., Ltd., Kobe, Japan

[21] Appl. No.: 70,201

[22] Filed: Jun. 2, 1993

[30] Foreign Application Priority Data

Jun. 12, 1992 [JP]  Japan .................................. 4-179296

[51] Int. Cl.⁶ ....................... G01N 33/48; G01N 21/00
[52] U.S. Cl. ...................................... 356/73; 356/317; 356/318; 356/336
[58] Field of Search .................. 356/72, 73, 317, 318, 356/39, 336; 250/574

[56] References Cited

U.S. PATENT DOCUMENTS

| 4,690,561 | 9/1987 | Ito | 356/73 |
| 5,159,397 | 10/1992 | Kosaka et al. | 356/73 |
| 5,159,398 | 10/1992 | Maekawa et al. | 356/73 |
| 5,159,642 | 10/1992 | Kosaka | 355/23 |
| 5,185,265 | 2/1993 | Steen et al. | 356/73 |
| 5,260,764 | 11/1993 | Fukuda et al. | 356/73 |
| 5,272,354 | 12/1993 | Kosaka | 356/336 |

*Primary Examiner*—William Mintel
*Assistant Examiner*—Minhloan Tran
*Attorney, Agent, or Firm*—Jones, Tullar & Cooper

[57] ABSTRACT

An imaging flow cytometer for capturing images and, analyzing particle components in a liquid sample containing particle components such as blood and urine, or microparticles such as organic high molecules in a suspension. A video camera of a vertical split scanning type is used in the optical system of a conventional particle imaging type flow cytometer. Using the video camera which is capable of scanning a certain limited range in the vertical direction repeatedly in one field period, the number of particles that can be imaged in unit time may be notably increased as compared with the case of using a conventional video camera. By thus constructing, in a flow cytometer possessing a still picture imaging function, the number of captured particles can be increased.

7 Claims, 7 Drawing Sheets

IMAGING FLOW CYTOMETER FOR IMAGING AND ANALYZING PARTICLE COMPONENTS IN A LIQUID SAMPLE

BACKGROUND OF THE INVENTION

The present invention relates to an imaging flow cytometer for imaging and analyzing particle components, such as blood and urine, or micro-particles such as organic high molecules in a suspension, in a liquid sample, and more particularly to an imaging flow cytometer capable of increasing the number of particles imaged by installing a vertical split scanning type video camera, in a flow cytometer provided with a still picture imaging function.

In a flow cytometer, in order to image particles flowing at a high speed of several meters per second in a flow cell, in the conventional method it was general, as shown in FIG. 1, to image deflection(deviation)-free particles by the combination of a pulse laser light source 29 capable of emitting an intense light only for a moment and an ordinary video camera 43.

In a flow cell 14, a sheath flow is formed by passing a sheath liquid around a sample fine flow 15 containing particles 16 to be analyzed, and a laser beam from an argon laser generator 10 is emitted to this sample fine flow 15, a light signal from the particle is detected by a photo detector (photomultiplier or the like) 22, and a signal S1 is sent to a signal processor 24. Thus, the particle is analyzed. The sheath flow is a flow formed by covering the surroundings of the suspension of particles with a laminar sheath liquid so that the particles may be aligned precisely to pass in a row in the middle of the liquid flow. Reference numeral S4 is a pulse emission trigger signal, 27 is a laser power source, 46 is an image processor, 12, 31 are condenser lenses, 20, 33 are objective lenses, 41 is a projection lens, and 18 is a beam stopper.

The Japanese Laid-open Patent Sho. 62-254037 discloses a flow cytometer provided with a streak imaging device, in which detection of particles and detection of particles by the imaging device are conducted almost simultaneously, and the imaging signal is processed only when matched with a predetermined characteristic value, that is, only the particle of specific characteristic is imaged. Using a high sensitivity camera and camera tube as the imaging device, a technique of momentary imaging of an entire image is also disclosed.

As disclosed in the Japanese Laid-open Patent Sho. 63-94156, in the flow cytometer, the light source for detecting particles is always lit, and passing of a cell is detected by a cell detector, and after a certain time delay in a delay circuit, an imaging laser pulse light source is emitted to image the cell.

In the method of the conventional apparatus disclosed in FIG. 1, however, the laser light source has a high coherency, and a coherence (interference) fringe is often obvious in the obtained particle image, and hence the image was not of high picture quality. When using an ordinary video camera 43, meanwhile, the number of particles that can be taken per unit time is about 30 at most (in the interlaced mode) to 60 (in the non-interlaced mode) if the particle concentration is low, and a sufficient number of images for the number of particles passing the detecting unit could not be obtained.

Neither patent referred to discloses an increase in the number of imaged particles by using the imaging means of a vertical split scanning type which is an important feature of the present invention.

OBJECTS AND SUMMARY OF THE PRESENT INVENTION

It is hence a primary object of the present invention to provide an imaging flow cytometer capable of obtaining a multiplicity (large number) of particle images per unit time (for example, 300 particles or more/sec at a maximum), by using imaging means for repetitively scanning a band-shaped region limited in a certain range in the vertical direction in one field period, in an optical system of a conventional particle imaging type flow cytometer.

It is other object of the present invention to provide an imaging flow cytometer capable of obtaining clear still images of particles flowing fast (for example, 5 m/sec or more) in a flow cell.

The imaging flow cytometer of the present invention combines the optical system of a conventional flow cytometer with a light source for illuminating particles and imaging means (for example, a video camera) capable of repetitively scanning a band shaped region limited in a certain range in the vertical direction in one field period. As a result, multiple (for example, 300 or more particles per second at a maximum) particle images can be obtained.

By furnishing this construction further with an image intensifier and/or laser light coherency lowering means (for example, an optical fiber), greater effects may be brought about.

To achieve the above objects, as shown in FIG. 2, the present invention provides an imaging flow cytometer, being a flow cytometer for passing a sheath liquid around a sample flow containing particles to be detected to form a sheath flow, irradiating a sample fine flow with light, and detecting light signals from the particles, comprising:

an irradiation light source for illuminating particles, imaging means for imaging particles by taking (picking up, capturing) particle transmission light images in the sample flow region, and an image processor for processing the images taken (picked up, captured) by the imaging means, wherein:

the imaging means is an imaging means of the split scanning type (vertically split scanning type) capable of repetitively scanning a band-shaped region B limited in a certain range of one screen region within one field period, and the particle flowing region is defined within the specific region (band-shaped region) B.

In another imaging flow cytometer of the present invention, in the above mentioned apparatus, means for detecting the incoming of a particle is provided, and the light for illuminating the particle is emitted according to the particle detection by the means for detecting incoming of a particle.

In a different imaging flow cytometer of the present invention, in the above mentioned apparatus, the light source for illuminating particles is a white light source, and an image intensifier for intensifying the particle transmission light image is disposed before (upstream of) the imaging means, and the image from the image intensifier is taken (picked up, captured) by the imaging means 38. As the image intensifier 38, it is preferred to employ an image intensifier with a shutter function of high speed response.

In still another imaging flow cytometer of the invention, in the above mentioned apparatus, the light source for illuminating particles is a pulse laser, and means for lowering the coherency of the laser light is provided. In this case, the image intensifier is not necessary.

DETAILED DESCRIPTION OF THE PREFERRED EMBODIMENTS

Figure 1:
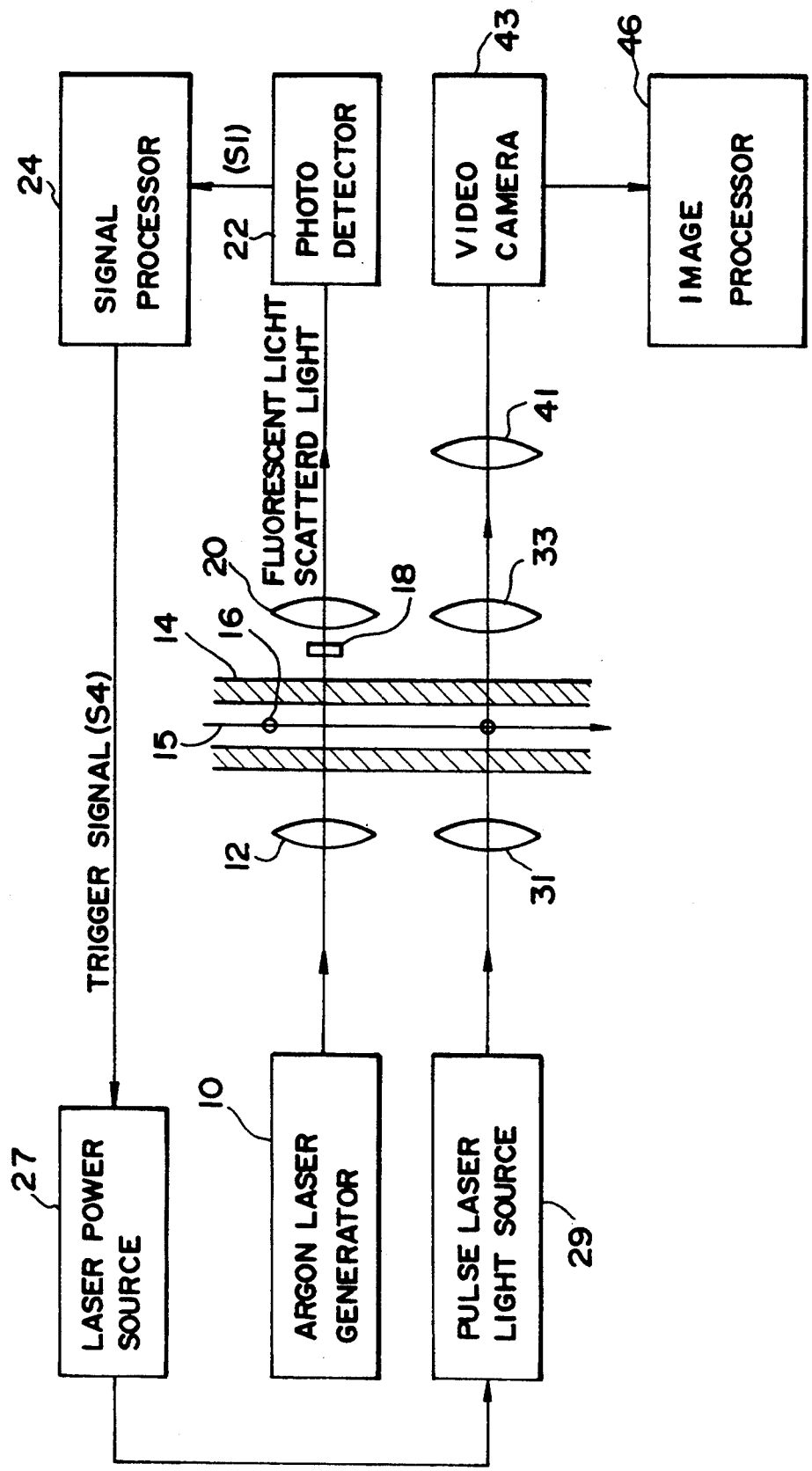
FIG. 1 is a schematic diagram of a conventional flow cytometer.

Referring now to the drawings, some of the preferred embodiments of the present invention are described in detail below.

In any embodiment, at a position in the downstream direction (a downward position in FIG. 2 and FIG. 3) of a detection area A2 for detecting scattered light and/or fluorescent light as in a conventional flow cytometer, a particle imaging area A1 is provided, and is designed to image by waiting until the particle reaches the imaging area A1 after passing of the particle in the detection area A2, which is illuminated with argon laser light.

EMBODIMENT 1

Figure 2:
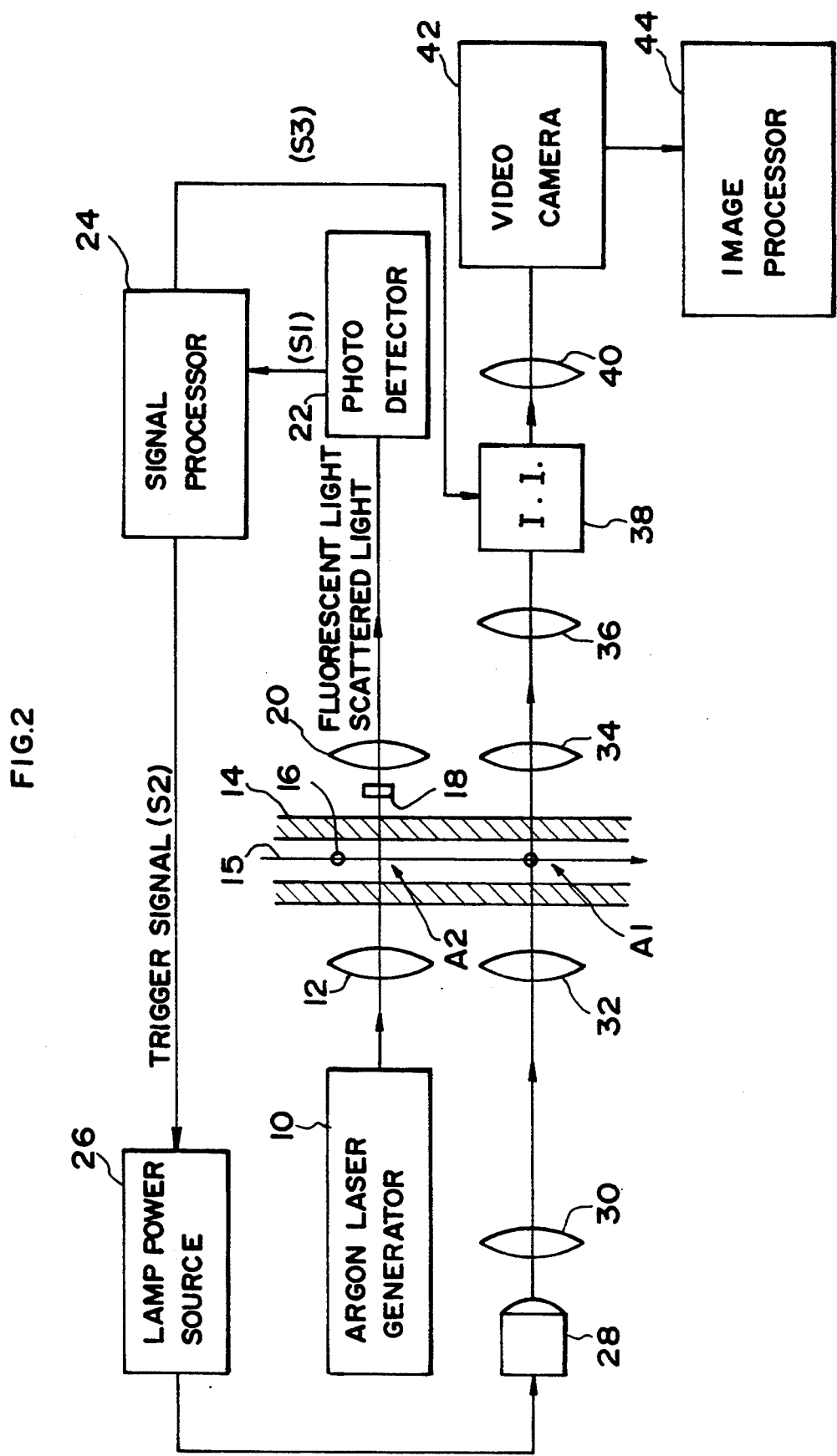
FIG. 2 is a schematic diagram showing an embodiment of an imaging flow cytometer of the present invention.

FIG. 2 shows an imaging flow cytometer in embodiment 1. A sample flow containing particles 16 to be detected is led into a flow cell 14, made of a transparent material such as glass or plastics, and a sheath liquid is supplied so as to cover the surroundings of the sample flow, and thus a sheath flow is formed. As an irradiation light source 28 for illuminating particles, a flash lamp or halogen lamp of normally emitting type is used, and an image intensifier (I.I.) 38 with a gate function is provided at the reception side, before a video camera 42. The video camera 42 is a vertical split scanning type video camera. This video camera is described later.

Figure 4:
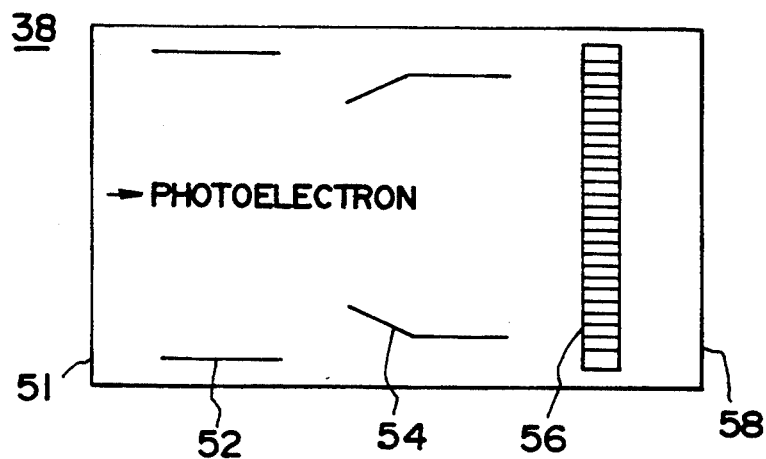
FIG. 4 is a block diagram for explaining the structure and operating principle of an image intensifier.

The gate function in the image intensifier (I.I.) 38 is generally realized by negative or positive control of the potential of the photoelectric plane to a microchannel plate (MCP) (see FIG. 4). More specifically, when the potential of the photoelectric plane 51 is positive, the photoelectrons released from the photoelectric plane 51 do not reach the MCP 56, namely the shutter (gate) is closed. On the contrary, when the potential of the photoelectric plane 51 is negative, the photoelectrons reach the MCP 56, namely the shutter (gate) is released (open). The response of this shutter function (gate function) is usually as fast as several nanoseconds to scores of nanoseconds. Reference numbers 52 and 54 are electronic lenses, and 58 is a fluorescent plane.

Supposing, for example, the flow velocity to be 5 m/sec, and the tolerance (allowance) range of image deflection to be 0.3 $\mu$m, the exposure time of the video camera to the CCD plane must be controlled to under 60 nsec (=0.3 $\mu$m/5 m/sec). A video camera realizing such a short shutter time is difficult at the present time, but it is easily realized by the image intensifier (I.I.) 38. That is, by controlling the gate ON time of the image intensifier (I.I.) 38 within 60 nsec, a particle image without deflection is obtained.

If taken by using an ordinary lamp and video camera in a short exposure time of less than 60 nsec, an almost black image only is obtained, but a bright particle image can be obtained by adding an image intensifier (I.I.) 38 with a photomultiplication factor of thousands to tens of thousands. Reference number 26 is a lamp power source, 32 is a condenser lens, 34 is an objective lens, 36 is a projection lens, 40 is a relay lens, S2 is a trigger signal from the signal processor 24 to the lamp power source 26, and S3 is a signal from the signal processor 24 to the image intensifier (I.I.) 38.

EMBODIMENT 2

Figure 3:
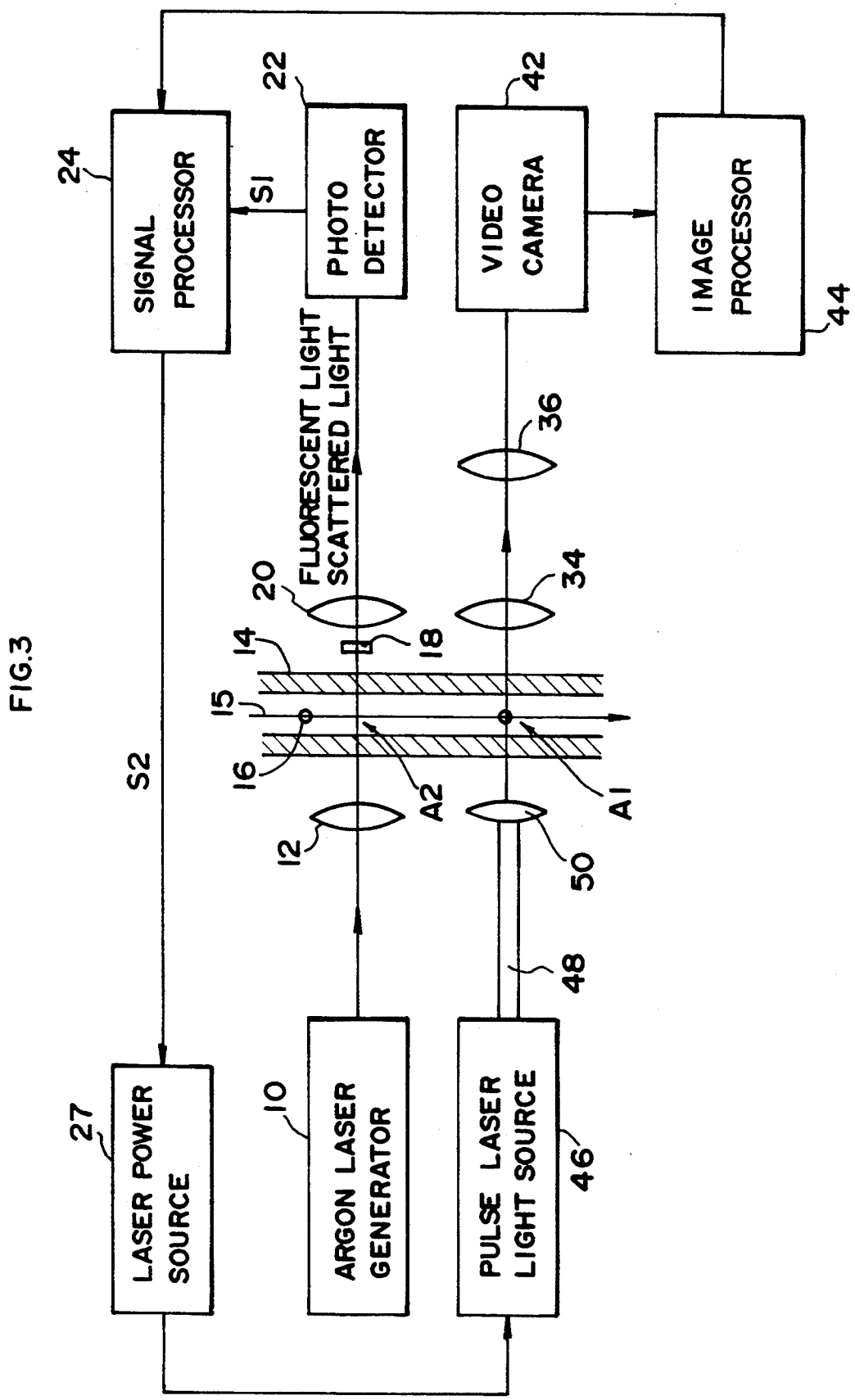
FIG. 3 is a schematic diagram showing another embodiment of an imaging flow cytometer of the present invention.

FIG. 3 shows an imaging flow cytometer in embodiment 2. As the irradiation light source for imaging particles, a laser light source 46 of a pulse emission type is used, and in order to lower the coherency, as far as possible, which is the characteristic of the laser light, the particle is illuminated through an optical fiber 48 so as to obtain a particle image with less obvious coherence (interference) fringe. Reference number 50 denotes a condenser lens.

It is easy to control one emission time of a pulse laser within 60 nsec, and the one emission energy is high and can be reduced to a high density, and therefore a sufficient irradiation intensity for imaging particles is obtained. Therefore, in this embodiment using the pulse laser light source 46 as the light source, the image intensifier (I.I.) 38 in Embodiment 1 (FIG. 2) is not needed.

The video camera 42 of the vertical split scanning type in Embodiments 1 and 2 is a video camera capable of repetitively scanning a band area B extending in the horizontal direction, limited in a certain range in the vertical direction of imaging area C, in one field period. For example, a multifunctional video camera model TM-640 of Takenaka System Equipment Co. is known.

Figure 6:
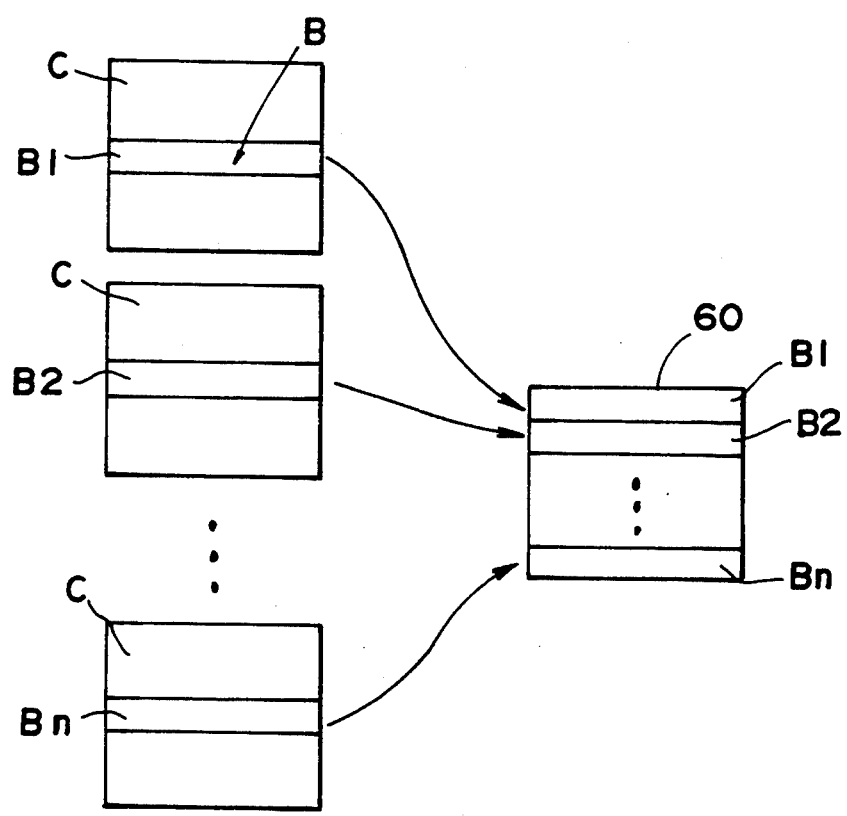
FIG. 6 is a block diagram of synthesized screen obtained in an imaging flow cytometer of the present invention.

FIG. 6 is a diagram for explaining the synthesis of screens of a plurality of specific regions into one by the vertical scanning type video camera 42. By matching slender band imaging areas B1, . . . with the flow of sheath sample flow, and repeating scanning in one field period (1/60 sec) of the video camera 42, a screen 60 synthesizing a plurality of screens of specific areas B1, . . . is obtained as a result of imaging as shown in FIG. 6.

Figure 7:
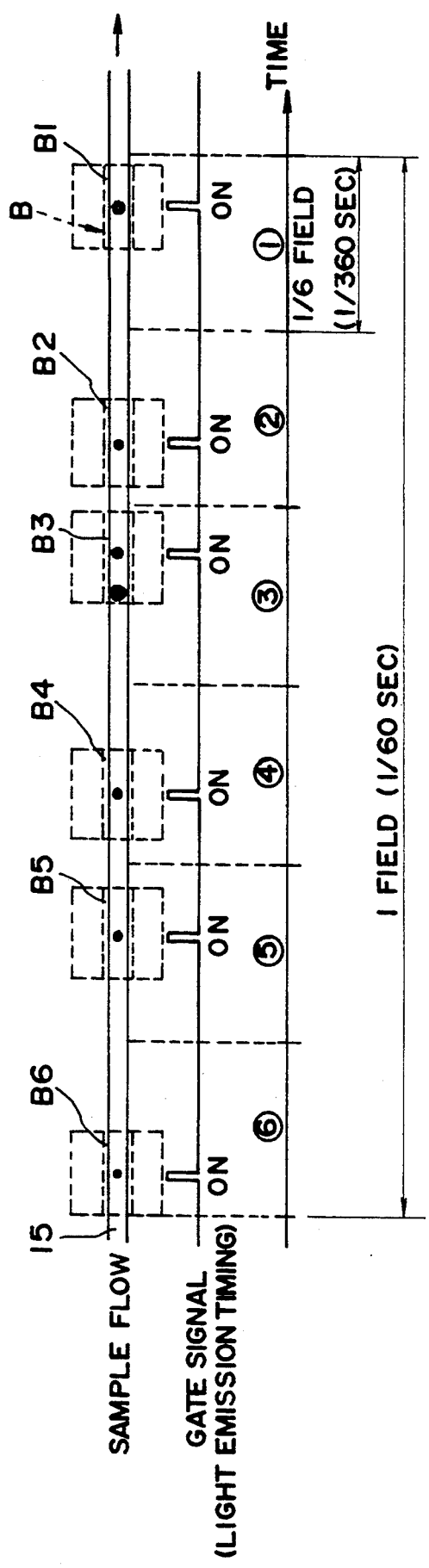
FIG. 7 is a diagram showing the relation of flow of particles and imaging timing of the present invention.

The relation between the particle flow and imaging areas B1, . . . is shown in FIG. 7. As shown in FIG. 7, the flowing direction of the sample flow 15 and the longitudinal direction of the imaging areas B1, . . . are matched, and the portion of the sample flow region 15 is adjusted within the imaging areas B1, . . . as shown in FIG. 7. The sample flow 15 is reduced to a thin (slender) flow, and the imaging areas B1, . . . are also slender, so that both can be matched favorably.

To divide one screen into six sections as in this embodiment, the imaging areas B1, . . . are taken once every 1/6 field period (1/360 sec) on average, and if at least one particle passes within 1/360 sec, the particle image can be taken securely. Actually, the number of particles that can be taken in unit time varies with the particle concentration, sheath width, sheath flow velocity, number of screen divisions, and other conditions, but about 300 particles can be imaged per second at a maximum. If measured for 30 seconds, about 10,000 particle images can be obtained at a maximum.

If the particle concentration is low or the sheath flow velocity is slow, the probability of particle passing in 1/360 sec is lower, and hence the number of particles taken per unit time also decreases. If, on the contrary, the particle concentration is high, exposure for the video camera is possible only once in 1/360 sec. In other words, if two or more particles pass within 1/360 sec, it is not possible to expose twice, three times or multiple times.

Figure 8:
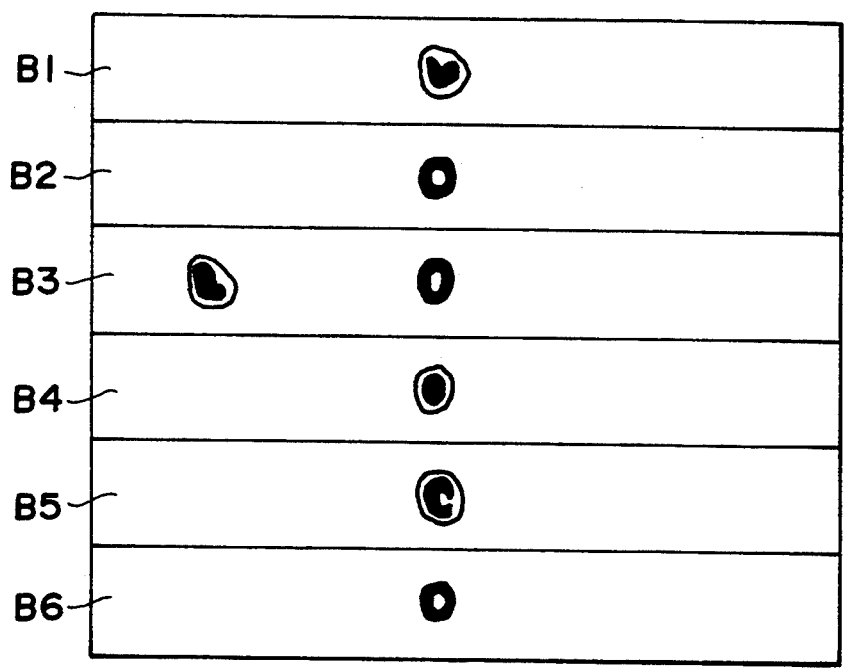
FIG. 8 is a diagram showing an example of synthesized screen obtained in an imaging flow cytometer of FIG. 7 of the present invention.

In this way, a synthetic screen as shown in FIG. 8 is obtained. In the divided screen B3 in FIG. 8, two particles are shown, which means two particles flowed closely to each other only by chance.

Figure 5:
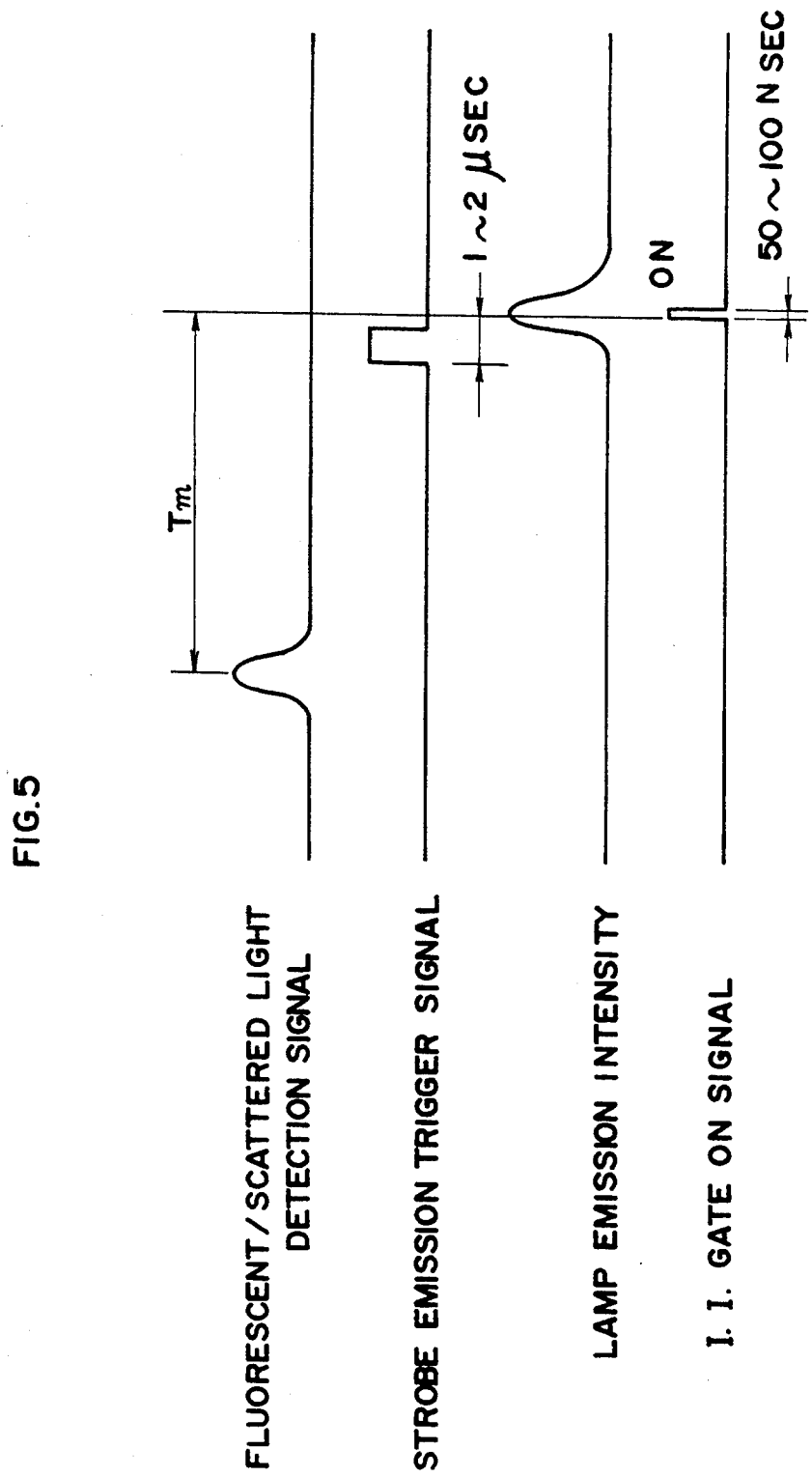
FIG. 5 is a wave form chart for explaining the timing of each signal in an imaging flow cytometer of the present invention.

FIG. 5 explains the emission timing control for imaging particles and turning on the gate of image intensifier (I.I.) 38, after detection of scattered light and/or fluorescence of particles obtained by the detection system of the conventional flow cytometer.

When a detection signal of scattered light and/or fluorescent light is obtained, passing of the particle in the detection area of the flow cell is detected by signal processing. Next, waiting until the particle reaches the video camera imaging area at a position in the downstream direction from the detection area, a trigger is applied to emit the flash lamp and/or pulse laser. When using a white light source, the image intensifier (I.I.) 38 is needed, and the gate of the image intensifier (I.I.) 38 is turned on for about scores of nanoseconds at this time. When using a lamp of the flash emission type, waiting until the emission intensity reaches a peak after triggering the lamp (about several microseconds), the gate of the image intensifier (I.I.) 38 is turned on. In FIG. 5, tm means the time required for the particle to move from the laser detection area to the imaging area of the video camera.

The time tm required for the particle to reach the imaging area from the detection area is determined by the distance between both areas and the sheath flow velocity, and in order to detect the particle securely in the middle of the divided screen, the sheath flow speed (velocity) should be stabilized, or the waiting time tm is corrected and controlled by recognizing the position of the particle image actually captured on the screen.

By turning on the gate of the image intensifier (I.I.) 38, the photoelectrons depending on the particle image focused (formed) on the photoelectric plane 50 are released, and the photoelectrons are fed into the MCP (microchannel plate) 56 to be amplified thousands of times. The amplified photoelectrons excite the fluorescent plane 58 which is the output plane, and particle images amplified thousands of times are obtained. The image of the fluorescent plane is focused (formed) on the CCD plane of the video camera 42 through the relay lens 40 or optical image fiber.

In the light receiving system in Embodiment 2 using the pulse laser light source 46 as the light source for irradiating particles, the image intensifier (I.I.) 38 is not needed, and the particle image is focused on the CCD plane of the video camera 42 through the objective lens 34 and projection lens 36, or optical image fiber.

Being thus constructed, the present invention brings about the following effects.

(1) Using the imaging means capable of repetitively scanning a certain limited range in the vertical direction in one field period, the number of particles that can be taken in a unit time can be significantly increased as compared with the case of using a conventional video camera.

(2) When a white light lamp is used as the light source for picking up the particle images, an image free of coherence (interference) fringe is obtained.

(3) When using a lamp and an image intensifier, a bright particle image without deflection can be obtained even at the sheath flow velocity of several meters/sec.

(4) When using a pulse emission type laser as a light source, the image intensifier is not needed, and a more compact construction is realized by using a semiconductor type pulse laser.

Having described preferred embodiments of the present invention with reference to the accompanying drawings, it is to be understood that the present invention is not limited to those precise embodiments, and that various changes and modifications may be effected thereby by one skilled in the art without departing from the scope or spirit of the present invention as defined in the appended claims.

What is claimed is:

1. An imaging flow cytometer for passing a sheath blow having a sheath liquid around a sample flow containing particles to be detected, irradiating a sample fine flow with light, and detecting light signals from the particles, comprising:
   an irradiation light source for illuminating particles in the sample fine flow,
   imaging means for imaging particles by receiving particle light images in a sample flow region of the sheath flow, and
   an image processor for processing the images taken by said imaging means, wherein:
   said imaging means is of the split scanning type capable of repetitively scanning a band-shaped scanning region of an imaging area limited to a certain range of the imaging area within one field period, and
   said sample flow region is defined within the band-shaped scanning region of the imaging area.

2. An imaging flow cytometer of claim 1, further comprising: means for detecting incoming of a particle, and wherein light for illuminating a particle is emitted according to particle detection by said means for detecting incoming of a particle.

3. An imaging flow cytometer of claim 2, further comprising:
   an image intensifier for intensifying the particle light image being disposed before said imaging means, the image from said image intensifier being taken by said imaging means, wherein the light source for illuminating particles is a white light source.

4. An imaging flow cytometer of claim 2, further comprising:
   means for lowering the coherency of the laser light, wherein the light source for illuminating particles is a pulse laser.

5. An imaging flow cytometer of claim 1, further comprising:
   an image intensifier for intensifying the particle light image being disposed before said imaging means, the image from said image intensifier being taken by said imaging means, wherein the light source for illuminating particles is a white light source.

6. An imaging flow cytometer of claim 1 further comprising:

means for lowering the coherency of the laser light, wherein the light source for illuminating particles is a pulse laser.

7. An imaging flow cytometer of claim 1, wherein the flow direction of the sample flow and the longitudinal direction of the band-shaped scanning region are matched.

* * * * *